United States Patent [19]
Oe et al.

[11] Patent Number: 5,006,520
[45] Date of Patent: Apr. 9, 1991

[54] FUSED PYRAZOLE COMPOUNDS AND PHARMACEUTICAL USE THEREOF

[75] Inventors: Takanori Oe, Nakatsu; Hiroyuki Sueoka, Buzen; Masao Hisadome, Nakatsu; Keiji Yamagami, Iruma, all of Japan

[73] Assignee: Yoshitomi Pharmaceutical Industries, Ltd., Osaka, Japan

[21] Appl. No.: 373,296

[22] PCT Filed: Oct. 11, 1988

[86] PCT No.: PCT/JP88/01034
§ 371 Date: Jun. 13, 1989
§ 102(e) Date: Jun. 13, 1989

[87] PCT Pub. No.: WO89/03385
PCT Pub. Date: Apr. 20, 1989

[30] Foreign Application Priority Data

Oct. 13, 1987 [JP] Japan .................. 62-257649
Jun. 7, 1988 [JP] Japan .................. 63-140147

[51] Int. Cl.$^5$ .................. A61K 31/435; C07D 471/04
[52] U.S. Cl. .................. 514/212; 514/218;
514/228.5; 514/231.5; 514/253; 514/303;
540/475; 540/597; 544/58.6; 544/61; 544/362;
546/119; 548/371; 548/372
[58] Field of Search .................. 546/119; 514/303, 212,
514/218, 228.5, 231.5, 253; 540/475, 597;
544/586, 61, 27, 362

[56] References Cited

U.S. PATENT DOCUMENTS 4,612,318  9/1986  Winters .................. 546/82
4,808,620  2/1989  Oe et al. .................. 546/119

FOREIGN PATENT DOCUMENTS 39-24818  11/1964  Japan .
39-24819  11/1964  Japan .

*Primary Examiner*—Bernard I. Bentz
*Attorney, Agent, or Firm*—Wenderoth, Lind & Ponack

[57] ABSTRACT

Novel fused pyrazole compounds of the general formula

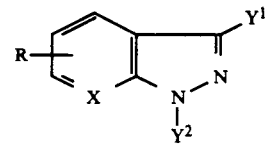

wherein all the symbols are as defined in the specification or its pharmaceutically acceptable salt which possesses a stimulating action on phagocytosis of leukocytes, a stimulating action on phagocytosis of macrophages, a restorative action on leukopenia, a stimulating action on non-specific resistance to infection, an antitumour action, an activating action on immune responses and the like, and thereof is of use as a pharmaceutical.

4 Claims, No Drawings

FUSED PYRAZOLE COMPOUNDS AND PHARMACEUTICAL USE THEREOF

TECHNICAL FIELD AND BACKGROUND ART

This invention relates to fused pyrazole compounds which are novel and useful as pharmaceuticals.

Heretofore, as fused pyrazole compounds, there have been described the indazole derivatives in Japanese Patent Application Laid-open (Kokai) No. 125281/1976 and pyrazolo[3,4-b]pyridine derivatives in U.S. Pat. No. 3,983,128 respectively.

Meanwhile, with the considerable developments of chemotherapeutic agents in the recent years, there has been seen remarkable progress in the therapy of infectious diseases. On the other hand, however, there have appeared new problems such as opportunistic infectious diseases on which the previous chemotherapeutic agents fail to effectively act and infectious diseases which result from leukopenia caused by the application of radiation-therapy or medicine-therapy to patients of cancers. For the purpose of the treatment of such infectious diseases, there have been desired not only the application of antibacterial agents but also the development of the medicines which are capable of recovering infection-phylactic action of feeble patients. However, success has not been attained.

DISCLOSURE OF THE INVENTION

For the purpose of developing infection-phylactic agents possessing as their main actions leukocytophagysthenic action and leukocyte multiplication action which seem to play the most important role at the initial stage of infection, the present inventors conducted intensive researches to find that the novel fused pyrazole compounds achieved the contemplated purpose, which resulted in the completion of this invention. That is, the present invention relates to the fused pyrazole compounds of the general formula

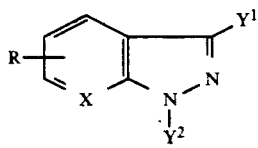

(I)

and their pharmaceutically acceptable salts.

In the above formula, X is $=$N- or $=$CH-, R represents hydrogen, an alkyl group, an alkoxy group or a halogen; $Y^1$ represents a group of the formula:

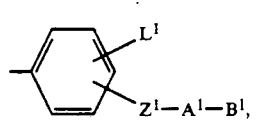

phenyl group or a phenyl group substituted by one to three halogen(s), alkyl group(s) and/or alkoxy group(s), and $Y^2$ represents a group of the formula:

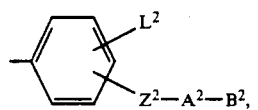

a group of the formula: $-A^2-B^2$, hydrogen, an alkyl group, a phenylalkyl group, a phenylalkyl group in which the phenyl nucleus is substituted by one to three halogen(s), alkyl group(s) and/or alkoxy group(s), phenyl group or a phenyl group substituted by one to three halogen(s), alkyl group(s) and/or alkoxy group(s), an alkoxyalkyl group, a hydroxyalkyl group, an alkoxycarbonylalkyl group, a carboxyalkyl group or an acyloxyalkyl group, wherein either $Y^1$ or $Y^2$ represents or both of $Y^1$ and $Y^2$ represent a group of the formula:

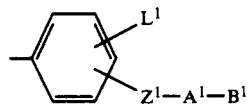

or of the formula

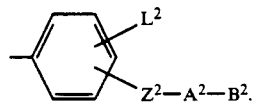

Herein, $Z^1$ and $Z^2$ are the same or different, and respectively represent $-O-$, $-S-$ or $-NR^3$ (wherein $R^3$ represents hydrogen or an alkyl group); $A^1$ and $A^2$ are the same or different, and respectively represent an alkylene group; $B^1$ and $B^2$ are the same or different, and respectively represent carboxyl group, an alkoxycarbonyl group, a phenylalkoxycarbonyl group (in which the phenyl neclesus may be substituted by one to three halogen(s), alkyl group(s), and/or alkoxy group(s)), an acyl group, hydroxy group, an acyloxy group or a group of the formula:

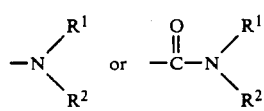

(wherein $R^1$ and $R^2$ are the same or different and respectively represent hydrogen, an alkyl group, a dialkylaminoalkyl group or a hydroxyalkyl group or represent a group which combinedly forms, together with the adjacent nitrogen atom, a heterocycle group) and $L^1$ and $L^2$ are the same or different and respectively represent hydrogen, a halogen, an alkyl group or an alkoxy group.

In this specification, the halogens include chlorine, bromine, fluorine and iodine and the alkyls mean straight- or branched-chain alkyls having 1-8 carbon atoms, which are exemplified by methyl, ethyl, propyl, isopropyl, butyl, isobutyl, tert-butyl, pentyl, isopentyl, hexyl and the like. The alkoxys mean straight- or branched-chain alkoxys having 1-8 carbon atoms, which are exemplified by methoxy, ethoxy, propoxy, isopropoxy, butoxy, isobutoxy, tert-butoxy, pentyloxy, isopentyloxy, hexyloxy and the like. The alkylene groups mean straight- or branched-chain alkylene groups having 1-8 carbon atoms, which are exemplified by methylene, ethylene, 1,1-dimethylethylene, trimethylene, propylene, 2-methyltrimethylene, 2-ethyltrimethylene, tetramethylene, pentamethylene, heptamethylene and the like. The phenylalkyl groups mean phenylalkyls in which the alkyls are straight- or branched-chain alkyls having 1-4 carbon atoms, which are exemplified by benzyl, 1-phenylethyl, 2-phenylethyl, 3-phenylpropyl, 4-phenylbutyl and the like and may be substituted on the phenyl ring by one to three halogen(s), straight- or branched-chain alkyl group(s) having 1-8 carbon atom(s) and/or straight- or branched-chain alkoxy group(s) having 1-8 carbon atom(s). The alkoxyalkyl groups are alkoxyalkyl groups in which the alkoxy groups and alkyl groups are respectively straight- or branched-chain alkoxys and alkyls having 1-4 carbon atoms, which are exemplified by 2-methoxyethyl, 2-ethoxyethyl, 3-methoxypropyl, 3-ethoxypropyl, methoxymethyl, 4-ethoxybutyl and the like. The hydroxyalkyls mean hydroxyalkyls in which the alkyls are straight- or branched-chain alkyls having 1-4 carbon atoms, which are exemplified by 2-hydroxyethyl, 2-hydroxypropyl, 3-hydroxypropyl, 2-hydroxy-1-methylethyl, 2,3-dihydroxypropyl and the like. The alkoxycarbonylalkyl groups mean alkoxycarbonylalkyls in which the alkoxy groups and the alkyl groups are respectively straight- or branched-chain alkoxys and alkyls having 1-4 carbon atoms, which are exemplified by methoxycarbonylmethyl, ethoxycarbonylmethyl, 2-methoxycarbonylethyl, 3-ethoxycarbonylpropyl and the like. The carboxyalkyl groups mean carboxyalkyls in which the alkyl groups are straight- or branched-chain alkyls having 1-4 carbon atoms, which are exemplified by carboxymethyl, 2-carboxyethyl, 1-carboxyethyl, 3-carboxypropyl and the like. The acyloxyalkyl groups mean acyloxyalkyls in which the acyl groups are straight- or branched-chain alkanoyls having 2-5 carbon atoms or benzoyl and the alkyl groups are straight- or branched-chain alkyls having 1-4 carbon atoms, which are exemplified by 2-acetyloxyethyl, 3-acetyloxypropyl, benzoylmethyl and the like. The dialkylaminoalkyl groups mean dialkylaminoalkyls in which the respective alkyl groups are straight- or branched-chain alkyls having 1-4 carbon atoms, which are exemplified by 2-dimethylaminoethyl, 2-diethylaminoethyl, 3-dimethylaminopropyl, 3-diethylaminopropyl and the like. The alkoxycarbonyl groups mean alkoxycarbonyls in which the alkoxy groups are straight- or branched-chain alkoxys having 1-4 carbon atoms, which are exemplified by methoxycarbonyl, ethoxycarbonyl, propoxycarbonyl, isopropoxycarbonyl, butoxycarbonyl, tert-butoxycarbonyl and the like The phenylalkoxycarbonyl groups are phenylalkoxycarbonyls in which the alkoxy groups are straight- or branched-chain alkoxys having 1-4 carbon atoms, which are exemplified by benzyloxycarbonyl, 2-phenylethoxycarbonyl, 3-phenylpropoxycarbonyl, 4-phenylbutoxycarbonyl and the like. The acyl groups mean straight- or branched-chain alkanoyls having 2-5 carbon atoms (e.g. acetyl, propionyl, butyryl, pivaloyl, valeryl) or benzoyl. The acyloxy groups are acyloxys in which the acyl groups are straight- or branched-chain alkanoyls having 2-5 carbon atoms or benzoyl, which are exemplified by acetoxy, propionyloxy, butyryloxy, pivaloyloxy, valeryloxy, benzoyloxy and the like. As the heterocyclic ring which $R^1$ and $R^2$ form combinedly, together with the adjacent nitrogen atom, there may be mentioned 5- to 7-membered ring which may have as another hetero atom at least one nitrogen optionally substituted by an alkyl group or hydroxyalkyl group, oxygen atom or sulfur, which are exemplified by 1-pyrrolidinyl, piperidino, 1-piperazinyl, 4-methyl-1-piperazinyl, morpholino, thiomorpholino, 4-ethyl-1-piperazinyl, 4-(2-hydroxyethyl)-1-piperazinyl, 1-homopiperazinyl, 4-methyl-1-homopiperazinyl, 2-oxo-1-pyrrolidinyl and the like.

As the pharmaceutically acceptable salts of the compounds of the general formula (I), mention may be made of acid addition salts such as hydrochlorides, sulfates, hydrobromides, phosphates, formates, acetates, fumarates, maleates, citrates, tartarates, malates, mandelates, methanesulfonates and toluenesulfonates; metal salts such as sodium salts, potassium salts, lithium salts, magnesium salts, calcium salts; amine salts, including quaternary ammonium salts, such as ammonium salts, triethylamine salts; salts of amino acids such as arginine salts, lysine salts, ornithine salts and so on. Besides, hydrates (monohydrate, ½ hydrate, 3/2 hydrate, etc.) and other solvates are also encompassed in this invention.

Preferred are the compounds of the above-mentioned general formula (I) wherein at least one of $Z^1$ and $Z^2$ is oxygen.

As the examples of the particularly preferable compounds of the general formula (I) and their pharmaceutically acceptable salts, mention may be made of the following compounds.

3-[4-(1-Methyl-2-dimethylaminoethoxy)phenyl]-1H-pyrazolo[3,4-b]pyridin-1-ylacetic acid;

ethyl 3-[4-(1-methyl-2-dimethylaminoethoxy)phenyl]-1H-pyrazolo[3,4-b]pyridin-1-ylacetate;

3-[4-(3-dimethylaminopropoxy)phenyl]-1H-pyrazolo[3,4-b]pyridin-1-ylacetic acid;

ethyl 3-[4-(2-dimethylaminoethoxy)phenyl]-1H-pyrazolo[3,4-b]pyridin-1-ylacetate;

1-[4-(3-dimethylaminopropoxy)phenyl]-3-phenyl-1H-pyrazolo[3,4-b]pyridine;

1-[3-(2-methyl-3-dimethylaminopropoxy)phenyl]-3-phenyl-1H-pyrazolo[3,4-b]pyridine;

1-(4-methylphenyl)-3-[4-(3-dimethylaminopropoxy)-phenyl]1H-pyrazolo[3,4-b]pyridine;

1-[3-(2-dimethylaminoethoxy)phenyl]-3-[4-(2-dimethylaminoethoxy)phenyl]-1H-pyrazolo[3,4-b]pyridine;

N-(2-diethylaminoethyl)-3-[3-(4-fluorophenyl)-1H-pyrazolo[3,4-b]pyridin-1-yl]phenoxyacetamide and 3-{3-[4-(3-dimethylaminopropoxy)phenyl]-1H-pyrazolo[3,4-b]pyridin-1-yl}propionic acid and their pharmaceutically acceptable salts.

The compounds of the general formula (I) of the present invention can be produced, for example, by the following methods.

(1) A method which comprises reacting a compound of the general formula

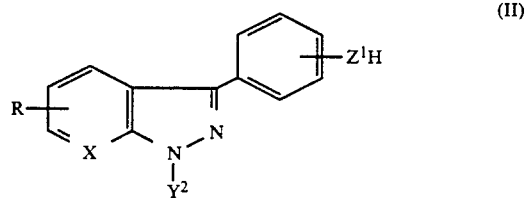

(II)

wherein all the symbols are of the same meanings as defined above with a compound of the general formula

(III)

wherein $X^1$ represents an easily-leaving group exemplified by a halogen such as chlorine or bromine or methanesulfonyloxy or p-toluenesulfonyloxy group and all the other symbols are as defined above; or reacting a compound of the general formula

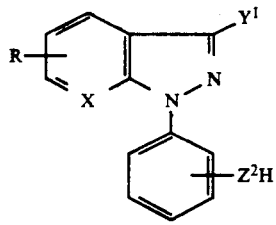
(IV)

wherein all the symbols are as defined above with a compound of the general formula $X^1-A^2-B^2$ (V)

wherein all the symbols are as defined above.

Among the compounds of the general formula (I), with regard to a compound of the general formula

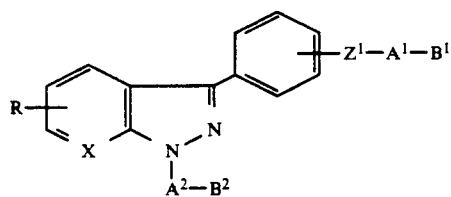
(VI)

wherein all the symbols are as defined above, but exclusively $-A^1-B^1$ and $-A^2-B^2$ are identical or a compound of the general formula

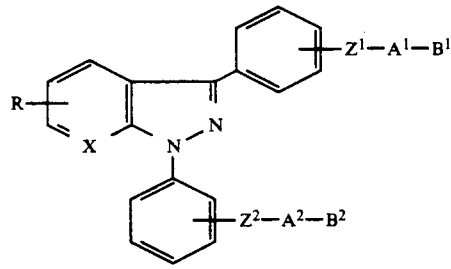
(VII)

wherein all the symbols are as defined above, they can also be produced by reacting a compound of the general formula

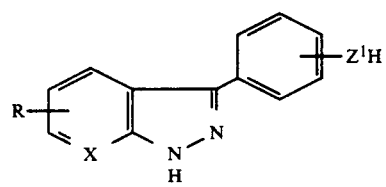
(VIII)

wherein all the symbols are as defined above or a compound of the general formula

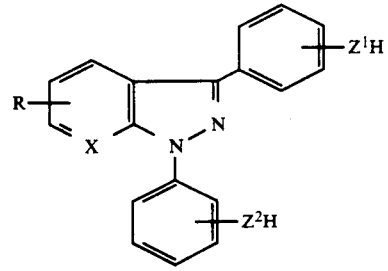
(IX)

wherein all the symbols are as defined above with a compound of the general formula (III).

The respective reaction conditions can be appropriately selected in accordance with the species of the substituents in the starting compounds. Preferably, the reactions proceed in a solvent inert to the reactions such as benzene, toluene, xylene, pyridine, ethanol, isopropylalcohol, ethylene glycol dimethyl ether, dimethylformamide or dioxane with the use of a deacidifying agent, if necessary, such as sodium hydroxide, sodium hydrogen carbonate, sodium carbonate, potassium carbonate or triethylamine at a temperature of 0° C. to 250° C.

Therein, among the starting compounds, for example, 1-(3-hydroxyphenyl)-3-phenyl-1H-pyrazolo[3,4-b]pyridine can be obtained by heating under reflux 2-chloro-3-benzoylpyridine and 3-methoxyphenylhydrazine in pyridine to obtain the corresponding hydrazone, and subjecting to ring-closure reaction the obtained hydrazone by heating under reflux in isopentyl alcohol with the use of potassium carbonate as a deacidifying agent to obtain 1-(3-methoxyphenyl)-3-phenyl-1H-pyrazolo[3,4-b]pyridine, followed by the elimination of the methoxy group thereof with the use of a butylmercaptanaluminium chloride system.

(2) A method which comprises subjecting a compound of the general formula

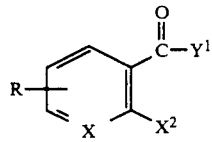
(X)

wherein $X^2$ represents a halogen such as fluorine, chlorine or bromine, and all the other symbols are as defined above, and a compound of the general formula $H_2NNH-Y^2$ (IX)

wherein $Y^2$ is as defined above to dehydration-condensation reaction to obtain a compound of the general formula

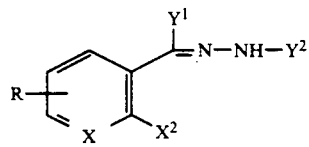
(XII)

and subjecting the compound of the general formula (XII) to ring-closure reaction.

The reaction conditions of the dehydration-condensation can be appropriately selected in accordance with the species of the substituents in the compounds (X) and (XI). Preferably, the dehydration-condensation reactions proceed in a solvent inert to the reactions such as benzene, toluene, xylene, pyridine, dioxane or diethylene glycol dimethyl ether with the use of a dehydrating agent, if necessary, such as molecular sieve or calcium chloride at a temperature of 50°–250° C. The ring-closure reactions proceed preferably in a solvent inert to the reactions such as pyridine, benzene, toluene, xylene, propanol, buthanol or pentanol with the use of a deacidifying agent, if necessary, such as sodium hydrogen carbonate, potassium carbonate, sodium carbonate, triethylamine or 2-aminopyridine at a temperature of 50°–250° C.

The objective compounds (I) can be, in some cases, obtained by reacting the compound (X) with the compound (XI) in a suitable solvent such as benzene, toluene, xylene, dioxane, diethylene glycol dimethyl ether or pyridine, if necessary, with the use of a suitable dehydrating agent or a deacidifying agent at a temperature of 100°–250° C. without isolating the compound (XII).

(3) A method which comprises reacting a compound of the general formula

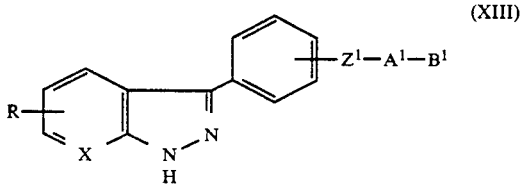

(XIII)

wherein all the symbols are as defined above with a compound of the general formula $X^1Y^3$         (XIV)

wherein $Y^3$ is a group of the formula: $-A^2-B^2$, an alkyl group, a phenylalkyl group, an alkoxyalkyl group, a hydroxyalkyl group, an alkoxycarbonylalkyl group, a carboxyalkyl group or an acyloxyalkyl group, and $X^1$ is as defined above.

The reaction conditions can be appropriately selected in accordance with the species of the substituents in the starting compounds. Preferably, the reactions proceed in a solvent inert to the reactions such as benzene, toluene, xylene, dimethylformamide, pyridine, chloroform, dichloromethane, dichloroethane, methanol or ethanol, if necessary, with the use of a deacidifying such as sodium hydroxide, potassium hydroxide, sodium carbonate, potassium carbonate or triethylamine at a temperature of 0° to 250° C.

(4) A method which comprises reacting a compound of the general formula

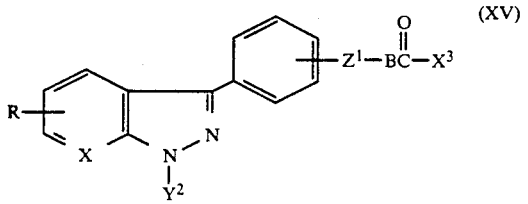

(XV)

wherein $X^3$ is an easily-leaving group such as hydroxyl group or a halogen, and all the other symbols are as defined above with a compound of the general formula

(XVI)

wherein all the symbols are as defined above, or reacting a compound of the general formula

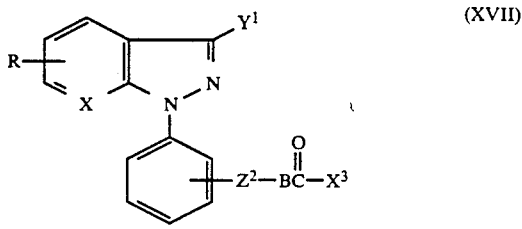

(XVII)

wherein all the symbols are as defined above with a compound of the general formula (XVI).

The reaction conditions can be appropriately selected in accordance with the species of the substituents in the starting compounds. Preferably, the reactions proceed in a solvent inert to the reactions such as chloroform, dichloromethane, dimethylformamide, dioxane, pyridine or toluene, if necessary, with the use of a deacidifying agent such as triethylamine, potassium carbonate, sodium carbonate or sodium hydrogen carbonate or a condensing agent such as dicyclohexylcarbodiimide or N,N'-carbonyldiimidazole or a reagent forming mixed acid anhydride such as ethyl chlorocarbonate or isopropyl chlorocarbonate at a temperature of 0°–200° C.

4-(1-Phenyl-1H-pyrazolo[3,4-b]pyridin-3-yl)phenoxyacetic acid can be produced by reacting 3-(4-hydroxyphenyl)-1-phenyl1H-pyrazolo[3,4-b]pyridine with ethyl bromoacetate in the presence of potassium carbonate as a deacidifying agent in dimethylformamide to obtain ethyl 4-(1-phenyl-1H-pyrazolo[3,4-b]pyridin-3-yl)phenoxyacetate, followed by hydrolysis thereof with the use of sodium hydroxide.

The compounds of the general formula (I) can be converted into the corresponding acid addition salts by the treatment with an organic acid or an inorganic acid such as hydrochloric acid, sulfuric acid, hydrobromic acid, phosphoric acid, formic acid, acetic acid, fumaric acid, maleic acid, citric acid, tartaric acid, malic acid, mandelic acid, methanesulfonic acid or toluenesulfonic acid by a conventional method.

Besides, in the case of the compounds of the general formula (I) which have carboxyl group, they can be, by a conventional method, converted into the corresponding salts thereof exemplified by metal salts such as sodium salts, potassium salts, lithium salts, magnesium salts and calcium salts, amine salts (including quaternary ammonium salts) such as ammonium salts and triethylamine salts and salts of amino acids such as arginine salts, lysine salts and ornitine salts.

The compounds of the general formula (I) and their pharmaceutically acceptable salts include those whose optical isomers exist. Both of the respective optical isomers and their mixtures are encompassed in this invention. The optically active isomers can be obtained by resolving the racemic isomers by a conventional means such as fractional crystallization or various chromatography or employing the optically active starting compound.

It has been shown that in various pharmacological experiments using subject animals suffering from diseases caused by immunodeficiency, the compounds of the present invention possess excellent stimulating effects on phagocytosis of leukocytes and macrophages, restorative effects on leukopenia, stimulating effects of non-specific resistance to infection, antitumor actions, activating effects on immune responses and the like. Accordingly, the compounds of the present invention can be used for the prophylaxis or therapy of leukopenia resulting from chemotherapy by anticancer agents and so on, infectious diseases resulting from postoperation, autoimmune diseases such as allergic diseases, lupus erythematosus and chronic articular rheumatism and cancers.

Below, the pharmacological actions of the compounds of the present inventions are specifically shown with the experimental methods.

Experimental Example 1

Stimulating effects on phagocytosis of leukocytes

The experiment was carried out in accordance with the method by Stossel et al [Journal of Clinical Investigation, vol. 51, p. 615 (1972)].

ICR mice weighing 30–35 g were intraperitoneally administered with glycogen. Two hours after administration, leukocytes in the abdominal cavity were collected. A suspension containing $5 \times 10^6$ leukocytes/ml was prepared. To 200 μl of the suspension, the test compounds and further 100 μl of mouse serum and 100 μl of non-viable yeasts ($1 \times 10^8$ particles/ml) were added. The mixture was incubated at 37° C. for 20 minutes. By observing about 200 leukocytes in the reaction mixture under a microscope of 400 magnifications, the leukocytes which phagocytized one or more non-viable yeasts were counted. The ratio of the number of phagocytic leukocytes treated with 0.1 μM of the test compounds added thereto relative to that of the phagocytic leukocytes of the control was estimated by the percentage.

Experimental Example 2

Restorative effects on leukopenia

ICR mice weighing 20–25 g were intraperitoneally administered with cyclophosphoramide at the dose of 200 mg/kg. On the following day after the administration, the test compounds were administered orally at the dose of 0.3 mg/kg or intravenously at the dose of 0.1 mg/kg. On the fourth day after the administration of cyclophosphoramide, the blood of the ICR mice was collected and the leukocyte count was measured by coulter counter. The ratio of the peripheral leukocyte count of mice treated with the test compounds relative to that of mice treated with cyclophosphamide was estimated by the percentage.

The results of the foregoing Experimental Examples 1 and 2 are shown in the following table.

TABLE 1

| Test compound | Stimulation effects on phagocytosis of leukocytes | Restorative effects on leukopenia | |
|---|---|---|---|
| | | Oral administration | intraveous administration |
| Compound of Example 1 | 173% | 171% | 172% |
| Compound of | 179% | 171% | 181% |

TABLE 1-continued

| Test compound | Stimulation effects on phagocytosis of leukocytes | Restorative effects on leukopenia | |
|---|---|---|---|
| | | Oral administration | intraveous administration |
| Example 3 Compound of Example 4 | 192% | 209% | 167% |
| Compound of Example 61 | 162% | 151% | 178% |
| Compound of Example 62(3) | 176% | 172% | 201% |

Experimental Example 3

Antitumor activity test

To male $CDF_1$ mice aged 8 weeks, $10^6$ IMC cancer cells (originated from Microbiological Chemistry Institute) were intraperitoneally transplanted. For consecutive 5 days from the day following transplantation the test compounds were intraperitoneally administered once a day. By observing survival of 3 or 6 mice per group and obtaining MST (Mean Survial Time), there was estimated T/C (%)=(MST of treated mice/MST of control) x 100.

The results are shown in the following table.

TABLE 2

| Test compound | T/C (%) | |
|---|---|---|
| | 50 mg/kg | 100 mg/kg |
| Compound of Example 1 | 114 | 243 |
| Compound of Example 3 | 212 | 304 |
| Compound of Example 4 | 239 | 268 |

Experimental Example 4

Acute toxicity test

The compound of Example 62(3) was orally and intraperitoneally administered to the mice at the dose of 1000 mg/kg and 300 mg/kg respectively. Incidence of death was not observed.

When the compounds of the general formula (I) or their pharmaceutically acceptable salts or solvates such as hydrate are used as pharmaceuticals, they can be orally or non-orally administered as they are or in such forms as tablets, capsules, powders and injections which are obtained by mixing them with pharmacologically acceptable suitable carriers, excipients, diluents and the like. While the dosage varies depending upon the target diseases, symptoms, age, administration route and so on, the daily dosage per adult man is about 10–500 mg in the case of oral administration and about 0.1–100 mg in the case of non-oral administration such as intravenous administration. They can be administered at said dosage once a day or in several times divided doses The present invention is in further detail described by Reference Examples for the preparation of the starting compounds and Examples for the preparation of the compounds of the present invention, which should not, needless to say, be construed to be limitative to the present invention.

Reference Example 1

In 300 ml of pyridine were dissolved 30 g of 2-chloro-3pyridyl-4-methoxyphenyl-ketone and 18 g of 4-methylphenylhydrazine. The solution was heated under reflux for 6 hours. The reaction mixture was concentrated under reduced pressure. Isopropyl ether was added thereto for crystallization to obtain 27.6 g of 2-chloro-3-pyridyl-4-methoxyphenyl-ketone-4-methylphenylhydrazone, m.p. 161°–163° C.

Reference Example 2

In 250 ml of isopentyl alcohol were suspended 27.6 g of 2-chloro-3-pyridyl-4-methoxyphenyl-ketone-4-methylphenylhydrazone and 27.6 g of potassium carbonate. The mixture was stirred under reflux for 16 hours. After the reaction mixture was concentrated under reduced pressure, the residue was extracted with chloroform-water. The organic layer was concentrated. Hexane was added to the residue for crystallization to give 17.7 g of 3-(4-methoxyphenyl)-1-(4-methylphenyl)1H-pyrazolo[3,4-b]pyridine, m.p. 143°–145° C.

Reference Example 3

In 250 ml of dichloromethane was suspended 22.4 g of anhydrous aluminium chloride. While stirring, 22.4 ml of butylmercaptan was added. After the mixture was stirred at room temperature for 1 hour, 17.7 g of 3-(4-methoxyphenyl)-1(4-methylphenyl)-1H-pyrazolo[3,4-b]pyridine was added thereto under ice-cooling. After the mixture was stirred at room temperature for 4 hours, the reaction mixture was poured into about 1 l of ice-water. The resulting crystals were collected by filtration, washed with water and recrystallized from methanol to give 13.8 g of 3-(4-hydroxyphenyl)-1-(4-methylphenyl)-1H-pyrazolo[3,4-b]pyridine, m.p. 201°–203° C.

Reference Example 4

In 40 ml of pyridine were dissolved 6.5 g of 2-chloro-3-pyridyl-phenyl-ketone and 4.2 g of 3-methoxyphenylhydrazine. The solution was heated under reflux for 15 hours. After the reaction mixture was concentrated under reduced pressure, hexane was added to the residue for crystallization to give 8.5 g of 2-chloro-3-pyridyl-phenyl-ketone-3-methoxyphenylhydrazone, m.p. 141°–143° C.

Reference Example 5

In 30 ml of isopentyl alcohol were suspended 4.3 g of 2-chloro-3-pyridyl-phenyl-ketone-3-methoxyphenylhydrazone and 4.3 g of potassium carbonate. The suspension was stirred under reflux for 18 hours. After the reaction mixture was concentrated under reduced pressure, the residue was extracted with chloroform-water. The organic layer was concentrated, and the residue was purified by silica gel chromatography (eluted by chloroform). Hexane was added for crystallization to give 2.1 g of 1-(3-methoxyphenyl)-3-phenyl-1H-pyrazolo[3,4-b]pyridine, m.p. 102°–105° C.

Reference Example 6

In 400 ml of dichloromethane was suspended 45.1 g of anhydrous aluminium chloride. While stirring, 45.1 ml of butylmercaptan was added thereto. After the mixture was stirred at room temperature for 1 hour, 34 g of 1-(3-methoxy- phenyl)-3-phenyl-1H-pyrazolo[3,4-b]pyridine was added under ice-cooling. The mixture was stirred at room temperature for 6 hours. The reaction mixture was poured into about 2 l of ice-water. The resulting crystals were collected by filtration, and washed with water to give 33.0 g of 1-(3-hydroxy- phenyl)-3-phenyl-1H-pyrazolo[3,4-b]pyridine, m.p. 142°–144° C.

In the same manner as in Reference Examples 1–6, the following compounds were obtained.

3-(4-Chlorophenyl)-1-(4-hydroxyphenyl)-1H-pyrazolo[3,4-b]pyridine, m.p. 186°–188° C.

1-(2-Hydroxyphenyl)-3-phenyl-1H-pyrazolo[3,4-b]pyridine, m.p. 125°–127° C.

3-(4-Hydroxyphenyl)-1-phenyl-1H-pyrazolo[3,4-b]pyridine, m.p. 178°–181° C.

3-(4-Chlorophenyl)-1-(3-hydroxyphenyl)-1H-pyrazolo[3,4-b]pyridine, m.p. 136°–138° C.

1-(3-Hydroxyphenyl)-3-(4-hydroxyphenyl)-1H-pyrazolo[3,4-b]pyridine, m.p. 152°–154° C.

3-(4-Fluorophenyl)-1-(3-hydroxyphenyl)-1H-pyrazolo[3,4-b]pyridine, m.p. 171°–173° C.

1-(4-Hydroxyphenyl)-3-phenyl-1H-pyrazolo[3,4-b]pyridine, m.p. 185°–186° C.

3-(4-Hydroxyphenyl)-1-methyl-1H-pyrazolo[3,4-b]pyridine, m.p. 193°–195° C.

3-(4-Fluorophenyl)-1-(3-hydroxyphenyl)-1H-indazole, m.p. 166°–167° C.

1-(3-Hydroxyphenyl)-3-phenyl-1H-indazole, m.p. 125°–127° C.

1-(3-Hydroxyphenyl)-6-methyl-3-phenyl-1H-pyrazolo[3,4-b]pyridine, m.p. 156°–158° C.

EXAMPLE 1

In 100 ml of dimethylformamide were suspended 7.0 g of 1-(4-hydroxyphenyl)-3-phenyl-1H-pyrazolo[3,4-b]pyridine, 3.6 g of 3-dimethylaminopropylchloride and 3.7 g of potassium carbonate. The mixture was stirred at 100° C. for 4 hours. After the solvent was distilled off under reduced pressure, the residue was extracted with chloroform-water. The organic layer was concentrated, and the residue was purified by silica gel column chromatography (eluent: chloroform : methanol=20:1). Thereafter, by adding maleic acid, the purified product was converted into the salt. The obtained crude crystals were recrystallized from ethyl acetate to give 7.2 g of 1-[4-(3-dimethylaminopropoxy)phenyl]-3-phenyl-1H-pyrazolo[3,4-b]pyridine·maleate, m.p. 133°–136° C.

EXAMPLE 2

In 60 ml of dimethylformamide were suspended 4.0 g of 3-(4-bromophenyl)-1-(4-hydroxyphenyl)-1H-pyrazolo[3,4-b]pyridine, 1.8 g of 2-diethylaminoethylchloride and 1.7 g of potassium carbonate. The mixture was stirred at 100° C. for 6 hours. After the solvent was distilled off under reduced pressure, the residue was extracted with toluene-water. The organic layer was concentrated. By adding maleic acid, the residue was corverted into the salt. The obtained crude crystals were recrystallized from ethyl acetate to give 3.0 g of 3-(4-bromophenyl)-1-[4-(2-diethylaminoethoxy)-phenyl]-1H-pyrazolo[3,4-b]pyridine·maleate, m.p. 135°–140° C.

EXAMPLE 3

In 70 ml of dimethylformamide were suspended 4.0 g of 1-(3-hydroxyphenyl)-3-phenyl-1H-pyrazolo[3,4-b]pyridine, 2.6 g of 3-dimethylamino-2-methylpropylchloride and 2.3 g of potassium carbonate. The mixture was stirred at 100° C. for 6 hours. The solvent was distilled off under reduced pressure. By adding maleic acid, the residue was converted into the salt. The obtained crude crystals were recrystallized from a mixed solvent of ethyl acetate and ethanol to give 5.2 g of 1-[3-(3-dimethylamino-2-methylpropoxy)phenyl]-3-phenyl-1H-pyrazolo[3,4-b]pyridine·maleate, m.p. 134°-136° C.

EXAMPLE 4

In 15 ml of dimethylformamide were suspended 4.5 g of 3-(4-hydroxyphenyl)-1-(4-methylphenyl)-1H-pyrazolo[3,4-b]pyridine, 2.2 g of 3-dimethylaminopropylchloride and 2.3 g of potassium carbonate. After the mixture was stirred at 100° C. for 4 hours, it was extracted with toluene-water. The organic layer was concentrated. By adding maleic acid to the residue, it was converted to the salt. The obtained crude crystals were recrystallized from ethanol to give 4.0 g of 3-[4-(3-dimethylaminopropoxy)phenyl]-1-(4-methylphenyl)-1H-pyrazolo[3,4-b]pyridine·maleate, m.p. 138°-140° C.

EXAMPLE 5

In 15 ml of dimethylformamide were suspended 5.3 g of 3-(4-fluorophenyl)-1-(3-hydroxyphenyl)-1H-indazole, 2.5 g of 3-dimethylaminopropylchloride and 2.7 g of potassium carbonate. The mixture was stirred at 100° C. for 4 hours, and then it was extracted with toluene-water. After the organic layer was concentrated, maleic acid was added to the residue to obtain the salt. The obtained crude crystals were recrystallized from ethyl acetate to give 5.0 g of 3-(4-fluorophenyl)-1-[3-(3-dimethylaminopropoxy)phenyl]-1H-indazole·maleate, m.p. 110°-112° C.

EXAMPLE 6

In 75 ml of dimethylformamide were suspended 5.0 g of 3-(4-fluorophenyl)-1-(3-hydroxyphenyl)-1H-pyrazolo[3,4-b]pyridine, 3.5 g of N,N-diethylbromoacetamide and 2.5 g of potassium carbonate. The mixture was stirred at 60° C. for 5 hours. After the solvent was distilled off under reduced pressure, the residue was extracted with ethyl acetate-water. The organic layer was concentrated. Isopropyl ether was added to the residue for crystallization. The obtained crude crystals were recrystallized from ethyl acetate to give 2.8 g of N,N-diethyl-3-[3-(4-fluorophenyl)-1H-pyrazolo[3,4-b]pyridin-1yl]phenoxyacetamide, m.p. 102°-105° C.

EXAMPLE 7

By conducting reactions and treatment in the same manner as in the above-mentioned Examples 1-6, using 1-(4-hydroxyphenyl)-3-phenyl-1H-pyrazolo[3,4-b]pyridine and 2-dimethylaminoethylchloride, there was obtained 1-[4-(2-dimethylaminoethoxy)phenyl]-3-phenyl-1H-pyrazolo[3,4-b]pyridinep·maleate, m.p. 123°-126° C.

EXAMPLE 8

By reacting and treating in the same manner as in the above-mentioned Examples 1-6, using 1-(4-hydroxyphenyl)-3-phenyl-1H-pyrazolo[3,4-b]pyridine and 4-dimethylaminobutylchloride, there was obtained 1-[4-(4-dimethylaminobutoxy)phenyl]-3-phenyl-1H-pyrazolo[3,4-b]pyridine·maleate, m.p. 112°-115° C.

EXAMPLE 9

By conducting reactions and treatments in the same manner as in the above-mentioned Examples 1-6, using 1-(4-hydroxphenyl)-3-phenyl-1-H-pyrazolo[3,4-b]pyridine and 2-diethylaminoethylchloride, there was obtained 1-[4-(2-diethylaminoethoxy)phenyl]-3-phenyl-1H-pyrazolo[3,4-b]pyridine·maleate, m.p. 110°-115° C.

EXAMPLE 10

By conducting reactions and treatments in the same manner as in the above-mentioned Examples 1-6, using 1-(4-hydroxyphenyl)-3-phenyl-1H-pyrazolo[3,4-b]pyridine and 3-dimethylamino-2-methylpropylchloride, there was obtained 1-[4-(3-dimethylamino-2-methylpropoxy)phenyl]-3-phenyl-1H-pyrazolo[3,4-b]pyridine·maleate, m.p. 143°-146° C.

EXAMPLE 11

By conducting reactions and treatments in the same manner as in Examples 1-6, using 3-(4-chlorophenyl)-1-(4-hydroxyphenyl)-1H-pyrazolo[3,4-b]pyridine and 3-dimethylaminopropylchloride, there was obtained 3-(4-chlorophenyl)-1-[4-(3-dimethylaminopropoxy)phenyl]-1H-pyrazolo[3,4-b]pyridine·maleate, m.p. 162°-165° C.

EXAMPLE 12

By conducting reactions and treatments in the same manner as in Examples 1-6, using 3-(4-bromophenyl)-1-(4-hydroxyphenyl)-1H-pyrazolo[3,4-b]pyridine and 3-dimethylaminopropylchloride, there was obtained 3-(4-bromophenyl)-1-[4-(3-dimethylaminopropoxy)phenyl]-1H-pyrazolo[3,4-b]pyridine·maleate, m.p. 162°-165° C.

EXAMPLE 13

By conducting reactions and treatments in the same manner as in Examples 1-6, using 1-(3-hydroxyphenyl)-3-phenyl-1H-pyrazolo[3,4-b]pyridine and 2-dimethylaminoethylchloride, there was obtained 1-[3-(2-dimethylaminoethoxy)phenyl]-3-phenyl-1H-pyrazolo[3,4-b]pyridine·2 maleate, m.p. 117°-120° C.

EXAMPLE 14

By conducting reactions and treatments in the same manner as in Examples 1-6, using 1-(3-hydroxyphenyl)-3-phenyl-1H-pyrazolo[3,4-b]pyridine and 3-dimethylaminopropylchloride, there was obtained 1-[3-(3-dimethylaminopropoxy)phenyl]-3-phenyl-1H-pyrazolo[3,4-b]pyridine·maleate, m.p. 120°-123° C.

EXAMPLE 15

By conducting reactions and treatments in the same manner as in Examples 1-6, using 1-(3-hydroxyphenyl)-3-phenyl-1H-pyrazolo[3,4-b]pyridine and 2-morpholinoethylchloride, there was obtained 1-[3-(2-morpholinoethoxy)phenyl]-3-phenyl-1H-pyrazolo[3,4-b]pyridine·maleate, m.p. 140°-142° C.

EXAMPLE 16

By conducting reactions and treatments in the same manner as in Examples 1-6, using 3-(4-chlorophenyl)-1-(3-hydroxyphenyl)-1H-pyrazolo[3,4-b]pyridine and 2-dimethylaminoethylchloride, there was obtained 3-(4-chlorophenyl)-1-[3-(2dimethylaminoethoxy)phenyl]-1H-pyrazolo[3,4-b]pyridine·maleate, m.p. 140°-143° C.

EXAMPLE 17

By conducting reactions and treatments in the same manner as in Examples 1-6, using 1-(2-hydroxyphenyl)-3-phenyl-1H-pyrazolo[3,4-b]pyridine and 2-dimethylaminoethyl chloride, there was obtained 1-[2-(2-dimethylaminoethoxy)phenyl]-3-phenyl-1H-pyrazolo[3,4-b]pyridine·maleate, m.p. 153°-157° C.

EXAMPLE 18

By conducting reactions and treatments in the same manner as in Examples 1–6, using 1-(2-hydroxyphenyl)-3-phenyl-1H-pyrazolo[3,4-b]pyridine and 3-dimethylaminopropylchloride, there was obtained 1-[2-(3-dimethylaminopropoxy)phenyl]-3-phenyl-1H-pyrazolo[3,4-b]pyridine·maleate, m.p. 123°–125° C.

EXAMPLE 19

By conducting reactions and treatments in the same manner as in Examples 1–6, using 3-(4-fluorophenyl)-1-(3-hydroxyphenyl)-1H-pyrazolo[3,4-b]pyridine and 2-piperidinoethylchloride, there was obtained 3-(4-fluorophenyl)-1-[3-(2-piperidinoethoxy)phenyl]-1H-pyrazolo[3,4-b]pyridine·maleate, m.p. 149°–151° C.

EXAMPLE 20

By conducting reactions and treatments in the same manner as in Examples 1–6, using 3-(4-fluorophenyl)-1-(3-hydroxyphenyl)-1H-pyrazolo[3,4-b]pyridine and 3-dimethylaminopropylchloride, there was obtained 3-(4-fluorophenyl)-1-[3-(3dimethylaminopropoxy)phenyl]-1H-pyrazolo[3,4-b]pyridine·maleate·½ hydrate, m.p. 102°–105° C.

EXAMPLE 21

By conducting reactions and treatments in the same manner as in Examples 1–6, using 3-(4-chlorophenyl)-1-(3-hydroxyphenyl)-1H-pyrazolo[3,4-b]pyridine and 3-dimethylamino-2-methylpropylchloride, there was obtained 3-(4-chlorophenyl)-1-[3-(3-dimethylamino-2-methylpropoxy)phenyl]-1H-pyrazolo-[3,4-b]pyridine·maleate, m.p. 150°–152° C.

EXAMPLE 22

By conducting reactions and treatments in the same manner as in Examples 1–6, using 1-(3-hydroxyphenyl)-3-phenyl-1H-pyrazolo[3,4-b]pyridine and 2-diethylaminoethylchloride, there was obtained 1-[3-(2-diethylaminoethoxy)phenyl]-3-phenyl-1H-pyrazolo[3,4-b]pyridine·maleate·½ hydrate, m.p. 86°–90° C.

EXAMPLE 23

By conducting reactions and treatments in the same manner as in Examples 1–6, using 3-(4-fluorophenyl)-1-(3-hydroxyphenyl)-1H-pyrazolo[3,4-b]pyridine and 3-piperidinopropylchloride, there was obtained 3-(4-fluorophenyl)-1-[3-(3-piperidinopropoxy)phenyl]-1H-pyrazolo[3,4-b]pyridine·fumarate, m.p. 73°–75° C.

EXAMPLE 24

By conducting reactions and treatments in the same manner as in Examples 1–6, using 3-(4-fluorophenyl)-1-(3-hydroxyphenyl)-1H-pyrazolo[3,4-b]pyridine and 3-dimethylamino-2-methylpropylchloride, there was obtained 3-(4-fluorophenyl)-1-[3-(3-dimethylamino-2-methylpropoxy)phenyl]-1H-pyrazolo[3,4-b]pyridine·maleate·½ hydrate, m.p. 128°–130° C.

EXAMPLE 25

By conducting reactions and treatments in the same manner as in Examples 1–6, using 3-(4-fluorophenyl)-1-(3-hydroxyphenyl)-1H-pyrazolo[3,4-b]pyridine and 3-dimethylaminopropylchloride, there was obtained 3-(4-fluorophenyl)-1-[3-(3-dimethylaminopropoxy)phenyl]-1H-pyrazolo[3,4-b]pyridine·maleate, m.p. 110°–112° C.

EXAMPLE 26

By conducting reactions and treatments in the same manner as in Examples 1–6, using 3-(4-chlorophenyl)-1-(3-hydroxyphenyl)-1H-pyrazolo[3,4-b]pyridine and 3-dimethylaminopropylchloride, there was obtained 3-(4-chlorophenyl)-1-[3-(3-dimethylaminopropoxy)phenyl]-1H-pyrazolo[3,4-b]pyridine·fumarate, m.p. 170°–172° C.

EXAMPLE 27

By conducting reactions and treatments in the same manner as in Examples 1–6, using 1-(3-hydroxyphenyl)-3-phenyl-1H-pyrazolo[3,4-b]pyridine and 4-dimethylaminobutylchloride, there was obtained 1-[3-(4-dimethylaminobutoxy)phenyl]-3-phenyl-1H-pyrazolo[3,4-b]pyridine·fumarate·monohydrate, m.p. 140°–143° C.

EXAMPLE 28

By conducting reactions and treatments in the same manner as in Examples 1–6, using 3-(4-hydroxyphenyl)-1-phenyl-1H-pyrazolo[3,4-b]pyridine and 3-dimethylaminopropylchloride, there was obtained 3-[4-(3-dimethylaminopropoxy)phenyl]-1-phenyl-1H-pyrazolo[3,4-b]pyridine·maleate, m.p. 132°–135° C.

EXAMPLE 29

By conducting reactions and treatments in the same manner as in Examples 1–6, using 3-(4-hydroxyphenyl)-1-phenyl-1H-pyrazolo[3,4-b]pyridine and 2-dimethylaminoethylchloride, there was obtained 3-[4-(2-dimethylaminoethoxy)phenyl]-1-phenyl-1H-pyrazolo[3 4-b]pyridine·maleate, m.p. 137°–141° C.

EXAMPLE 30

By conducting reactions and treatments in the same manner as in Examples 1–6, using 3-(4-fluorophenyl)-1-(3-hydroxyphenyl)-1H-pyrazolo[3,4-b]pyridine and 4-chloroacetylmorpholine, there was obtained 4-{3-[3-(4-fluorophenyl)-1H-pyrazolo[3,4-b]pyridin-1-yl]phenoxyacetyl}morpholine, m.p. 141°–143° C.

EXAMPLE 31

By conducting reactions and treatments in the same manner as in Examples 1–6, using 3-(4-hydroxyphenyl)-1-(4-methylphenyl)-1H-pyrazolo[3,4-b]pyridine and 3-dimethylamino-2-methylpropylchloride, there was obtained 1-(4-methylphenyl)-3-[4-(3-dimethylamino-2-methylpropoxy)phenyl]-1H-pyrazolo[3,4-b]pyridine·maleate, m.p. 170°–171° C.

EXAMPLE 32

By conducting reactions and treatments in the same manner as in Examples 1–6, using 3-(4-hydroxyphenyl)-1-methyl-1H-pyrazolo[3,4-b]pyridine and 3-dimethylaminopropylchloride, there was obtained 1-methyl-3-[4-(3-dimethylaminopropoxy)phenyl]-1H-pyrazolo[3,4-b]pyridine·maleate, m.p. 128°–129° C.

EXAMPLE 33

By conducting reactions and treatments in the same manner as in Examples 1–6, using 1-(3-hydroxyphenyl)-6-methyl-3-phenyl-1H-pyrazolo[3,4-b]pyridine and 3-dimethylamino-2-methylpropylchloride, there was obtained 6-methyl-1-[3-(3-dimethylamino-2-methylpropoxy)phenyl]-3-phenyl-1H-pyrazolo[3,4-b]pyridine·maleate, m.p. 123°–125° C.

EXAMPLE 34

By conducting reactions and treatments in the same manner as in Examples 1-6, using 1-(3-hydroxyphenyl)-3-phenyl-1H-indazole and 3-dimethylamino-2-methylpropylchloride, there was obtained 1-[3-(3-dimethylamino-2-methylpropoxy)phenyl]-3-phenyl-1H-indazole·maleate·2/5 ethyl acetate solvate, m.p. 58°-63° C.

EXAMPLE 35

By reacting in the same manner as in Example 1, using 4 g of 1-(4-hydroxyphenyl)-3-phenyl-1H-pyrazolo[3,4-b]pyridine and 3.6 g of 3-chloropropanol and recrystallizing the obtained crude crystals from ethyl acetate-isopropyl ether, there was obtained 1-[4-(3-hydroxypropoxy)phenyl]-3-phenyl-1H-pyrazolo[3,4-b]pyridine, m.p. 135°-138° C.

EXAMPLE 36

In 60 ml of chloroform were dissolved 6.0 g of 4-(1-phenyl-1H-pyrazolo[3,4-b]pyridin-3-yl)phenoxyacetic acid and 2.1 g of triethylamine. To the solution was added 2.3 g of ethyl chlorocarbonate at −30° C. The mixture was stirred for 30 minutes. Thereafter, 1.9 g of N,N-dimethylethylenediamine was further added. The temperature was gradually elevated to room temperature, and then the mixture was stirred at room temperature for 3 hours. The reaction mixture was extracted with chloroform, and purified by silica gel column chromatography (eluent: chloroform : methanol=25:1). By adding maleic acid thereto, the product was converted into the salt. The obtained crude crystals were recrystallized from ethyl acetate to give 3.9 g of N-(2-dimethylaminoethyl)-4-(1-phenyl-1H-pyrazolo[3,4-b]pyridin-3-yl)phenoxyacetamide·maleate, m.p. 169°-171° C.

EXAMPLE 37

In 60 ml of chloroform were dissolved 4.0 g of 3-[3-(4-fluorophenyl)-1H-pyrazolo[3,4-b]pyridin-1-yl]phenoxyacetic acid and 1.3 g of triethylamine. Thereto, 1.4 g of ethyl chlorocarbonate was added at −40° C. The mixture was stirred for 30 minutes. After 0.8 g of ethanolamine was added thereto, the temperature was gradually elevated to room temperature, and the mixture was stirred at room temperature for 2 hours. The reaction mixture was extracted with chloroform. The organic layer was concentrated. The obtained white crude crystals were recrystallized from dioxane to give 2.4 g of N-(2-hydroxyethyl)-3-[3-(4-fluorophenyl)-1H-pyrazolo[3,4-b]-pyridin-1-yl]phenoxyacetamide, m.p. 161°-163° C.

EXAMPLE 38

By conducting reactions and treatments in the same manner as in Examples 36 and 37, using 3-[3-(4-fluorophenyl)-1H-pyrazolo[3,4-b]pyridin-1-yl]phenoxyacetic acid and 2-diethylaminoethylchloride, there was obtained N-(2-diethylaminoethyl)-3-[3-(4-fluorophenyl)-1H-pyrazolo[3,4-b]pyridin-1-yl]phenoxyacetamide, m.p. 137°-138° C.

EXAMPLE 39

By conducting reactions and treatments in the same manner as in Examples 36 and 37, using 3-[3-(4-fluorophenyl)-1H-pyrazolo[3,4-b]pyridin-1-yl]phenoxyacetic acid and 4-methylpiperazine, there was obtained 1-{3-[3-(4-fluorophenyl)-1H-pyrazolo[3,4-b]pyridin-1-yl]phenoxyacetyl}-4-methylpiperazine, m.p. 132°-135° C.

EXAMPLE 40

By conducting reactions and treatments in the same manner as in Examples 36 and 37, using 4-(1-phenyl-1H-pyrazolo[3,4-b]pyridin-3-yl)phenoxyacetic acid and 2-diethylaminoethylamine, there was obtained N-(2-diethylaminoethyl)-4-(1-phenyl-1H-pyrazolo[3,4-b]pyridin-3-yl)phenoxyacetamide·fumarate, m.p. 152°-154° C.

EXAMPLE 41

By conducting reactions and treatments in the same manner as in Examples 36 and 37, using 4-(1-phenyl-1H-pyrazolo[3,4-b]pyridin-3-yl)phenoxyacetic acid and 4-methylpiperazine, there was obtained 4-methyl-1-[4-(1-phenyl-1H-pyrazolo[3,4-b]pyridin-3-yl)phenoxyacetyl]piperazine·maleate, m.p. 187°-189° C.

EXAMPLE 42

In 20 ml of pyridine were dissolved 3.0 g of 2-chloro-3-[4-(3-dimethylaminopropoxy)benzoyl]pyridine and 1 ml of hydrazine·monohydrate. The solution was heated under reflux for 18 hours. After the solvent was distilled off, water was added to the residue. The resulting crystals were collected by filtration and recrystallized from ethanol to give 1.2 g of 3-[4-(3-dimethylaminopropoxy)phenyl]-1H-pyrazolo[3,4-b]pyridine, m.p. 176°-177° C.

EXAMPLE 43

By conducting reactions and treatments in the same manner as in Example 42, using 17 g of 2-chloro-3-[4-(2-dimethylaminoethylamino)benzoyl]pyridine and 8.4 g of hydrazine·monohydrate, and recrystallizing the obtained crude crystals from ethyl acetate-methanol, there was obtained 3-[4-(2-dimethylaminoethylamino)phenyl]-1H-pyrazolo[3,4-b]pyridine, m.p. 165°-167° C.

EXAMPLE 44

By conducting reactions and treatments in the same manner as in Example 42, using 5.8 g of 2-chloro-3-[4-(2-dimethylaminoethylamino)benzoyl]pyridine and 1.2 g of methylhydrazine, converting into the maleate and recrystallizing from ethyl acetate, there was obtained 1-methyl-3-[4-(2-dimethylaminoethylamino)phenyl]-1H-pyrazolo[3,4-b]pyridine·maleate, m.p. 88°-90° C.

EXAMPLE 45

By conducting reactions and treatments in the same manner as in Example 40, using 68 g of 2-chloro-3-[4-(2-dimethylaminoethoxy)benzoyl]pyridine and 25 ml of hydrazine·monohydrate, and recrystallizing the obtained crude crystals from hydrous methanol, there was obtained 22 g of 3-[4-(2-dimethylaminoethoxy)phenyl]-1H-pyrazolo[3,4-b]pyridine, m.p. 132°-134° C.

EXAMPLE 46

In 20 ml of dimethylformamide were suspended 6.0 g of 3-[4-(3-dimethylaminopropoxy)phenyl]-1H-pyrazolo[3,4-b]pyridine and 4.1 g of potassium carbonate. While the mixture was stirred under heating at 50° C., 3.9 g of 4-chlorobenzylchloride dissolved in 5 ml of toluene was added. After the mixture was stirred at 50° C. for 1 hour, the mixture was extracted with toluene-water. The organic layer was concentrated. By adding maleic acid to the residue, the salt was obtained. The obtained crude crystals were recrystallized from ethanol to give 4.5 g of 1-(4-chlorobenzyl)-3-[4-(3-dimethylaminopropoxy)phenyl]-1H-pyrazolo[3,4-b]pyridine·maleate, m.p. 136°–138° C.

EXAMPLE 47

In dimethylformamide were suspended 5.6 g of 3-[4-(2-dimethylaminoethoxy)phenyl]-1H-pyrazolo[3,4-b]pyridine and 4.1 g of potassium carbonate. The mixture was stirred at 50° C. A solution of 5.0 g of 2-methoxymethyl p-toluenesulfonate dissolved in 5 ml of toluene was added dropwise over the period of 1.5 hours. After the mixture was stirred at 50° C. for 4 hours, it was extracted with toluene-water. By adding maleic acid, the salt was obtained. The obtained salt was recrystallized from ethyl acetate to give 1.8 g of 3-[4-(2-dimethylaminoethoxy)phenyl]-1-(2-methoxyethyl)-1H-pyrazolo[3,4-b]pyridine maleate, m.p. 115°–117° C.

EXAMPLE 48

In 5 ml of methanol was dissolved 0.55 g of metal sodium. Thereto, a solution of 3.0 g of 3-[4-(3-dimethylaminopropoxy)phenyl]-1H-pyrazolo[3,4-b]pyridine dissolved in 15 ml of dimethylformamide was added. While stirring at 10° C., 3.2 g of N,N-dimethyl-2-chloroacetamide was added. The mixture was stirred at room temperature for 3 hours. After the extraction with toluene-water, maleic acid was added to give the salt. The obtained crude crystals were recrystallized from ethanol to give 1.5 g of N,N-dimethyl-3-[4-(3-dimethylaminopropoxy)phenyl]-1H-pyrazolo[3,4-b]pyridine-1-ylacetamide·maleate, m.p. 165°–167° C.

EXAMPLE 49

By conducting reactions and treatments in the same manner as in Examples 46 and 48, using 3-[4-(2-dimethylaminoethoxy)phenyl]-1H-pyrazolo[3,4-b]pyridine and 2,4-dichlorobenzylchloride, there was obtained 1-(2,4-dichlorobenzyl)-3-[4-(2-dimethylaminoethoxy)phenyl]-1H-pyrazolo[3,4-b]pyridine·maleate, m.p. 136°–138° C.

EXAMPLE 50

By conducting reactions and treatments in the same manner as in Examples 46–48, using 3-[4-(3-dimethylaminopropoxy)phenyl]-1H-pyrazolo[3,4-b]pyridine and butylbromide, there was obtained 1-butyl-3-[4-(3-dimethylaminopropoxy)phenyl]1H-pyrazolo[3,4-b]pyridine·maleate, m.p. 112°–113° C.

EXAMPLE 51

By conducting reactions and treatments in the same manner as in Examples 46 and 48, using 3-[4-(3-dimethylaminopropoxy)phenyl]-1H-pyrazolo[3,4-b]pyridine and ethyl chloroacetate, there was obtained ethyl 3-[4-(3-dimethylaminopropoxy)phenyl]-1H-pyrazolo[3,4-b]pyridin-1-ylacetate·maleate, m.p. 108°–110° C.

Example 52

The crude crystals obtained by conducting reactions and treatments in the same manner as in Example 46 with the use of 5 g of 3-[4-(3-dimethylaminopropoxy)-phenyl]-1H-pyrazolo-[3,4-b]pyridine and 2.1 g of chloroacetone were recrystallized from ethyl acetate to give 1-acetonyl-3-[4-(3-dimethylaminopropoxy)phenyl]-1H-pyrazolo[3,4-b]pyridine·maleate, m.p. 119°–121° C.

Example 53

By conducting reactions and treatments in the same manner as in Example 52, using 3-[4-(3-dimethylaminopropoxy)phenyl]-1H-pyrazolo[3,4-b]pyridine and 2-chloro-4'-fluoroacetophenone, there was obtained 1-(4-fluorophenacyl)-3-[4-(3-dimethylaminopropoxy)-phenyl]-1H-pyrazolo[3,4-b]pyridine·3/2 fumarate, m.p. 165°–169° C.

EXAMPLE 54

By conducting reactions and treatments in the same manner as in Example 46, using 6 g of 3-[4-(3-dimethylaminoethylamino)phenyl]-1H-pyrazolo[3,4-b]pyridine and 2-chlorobenzyl chloride, and converting into the fumarate, followed by recrystallization from ethanol, there was obtained 1-(2-chlorobenzyl)-3-[4-(2-dimethylaminoethylamino)phenyl]-1H-pyrazolo[3,4-b]pyridine·fumarate, m.p. 155°–157° C.

EXAMPLE 55

In 100 ml of dimethylformamide were suspended 5.0 g of 3-(4-hydroxyphenyl)-1H-pyrazolo[3,4-b]pyridine, 4.1 g of 2-dimethylaminoethyl chloride and 5.3 g of potassium carbonate. The mixture was stirred at 100° C. for 3 hours. The solvent was distilled off under reduced pressure. The residue was extracted with toluene-water and purified by silica gel column chromatography (eluent: chloroform : methanol=20:1). Maleic acid was added to give the salt. The obtained crude crystals were recrystallized from a mixed solvent of ethyl acetate-ethanol to give 1.7 g of 1-(2-dimethylaminoethyl)-3-[4-(2-dimethylaminoethoxy)phenyl]-1H-pyrazolo[3,4-b]pyridine·2 maleate, m.p. 96°–98° C.

EXAMPLE 56

In 300 ml of dimethylformamide were suspended 20.0 g of 1-(3-hydroxyphenyl)-3-(4-hydroxyphenyl)-1H-pyrazolo[3,4-b]pyridine, 20.1 g of 3-dimethylaminopropylchloride and 22.8 g of potassium carbonate. The mixture was stirred at 90° C. for 4 hours. After the solvent was distilled off, the residue was extracted with toluene-water and purified by silica gel column chromatography (eluent: silica gel methanol=5:1). Thereafter, fumaric acid was added to give the salt. The obtained crude crystals were recrystallized from a mixed solvent of ethyl acetate and methanol to give 8.0 g of 1-[3-(3-dimethylaminopropoxy)phenyl]-3-[4-(3-dimethylaminopropoxy)phenyl]-1H-pyrazolo[3,4-b]pyridine·2 fumarate, m.p. 145°–148° C.

EXAMPLE 57

By conducting reactions and treatments in the same manner as in Examples 55 and 56, using 3-(4-hydroxyphenyl)-1H-pyrazolo[3,4-b]pyridine and 3-dimethylpropylchloride, there was obtained 1-(3-dimethylaminopropyl)-3-[4-(3-dimethylaminopropoxy)-phenyl]-1H-pyrazolo[3,4-b]pyridine·2 maleate, m.p. 127°–130° C.

EXAMPLE 58

By conducting reactions and treatments in the same manner as in Examples 55 and 56, using 1-(3-hydroxyphenyl)-3-(4-hydroxyphenyl)-1H-pyrazolo[3,4-b]pyridine and 2-dimethylaminoethylchloride, there was obtained 1-[3-(2-dimethylaminoethoxy)phenyl]-3-[4-(2-dimethylaminoethoxy)phenyl]-1H-pyrazolo[3,4-b]pyridine·2 fumarate, m.p. 115°–118° C.

Below, mention is made of the compounds which can be produced in the same manner as in the foregoing Examples.

1-(4-Methylphenyl)-3-[4-(2-dimethylamino-1-methylethoxy)phenyl]-1H-pyrazolo[3,4-b]pyridine·maleate, m.p. 139°–140° C.

6-Methyl-1-(4-methylphenyl)-3-[4-(3-dimethylaminopropoxy)phenyl-1H-pyrazolo[3,4-b]pyridine 6-Methyl-1-(4-methylphenyl)-3-[4-(3-dimethylamino-2-methylpropoxy)phenyl]-1H-pyrazolo[3,4-b]pyridine 1-(3-Methylphenyl)-3-[4-(3-dimethylaminopropoxy)phenyl]-1H-pyrazolo[3,4-b]pyridine 1-(3-Methylphenyl)-3-[4-(3-dimethylamino-2-methylpropoxy)phenyl]-1H-pyrazolo[3,4-b]pyridine 1-(2-Methylphenyl)-3-[4-(3-dimethylaminopropoxy)phenyl]-1H-pyrazolo[3,4-b]pyridine 1-(2-Methylphenyl)-3-[4-(3-dimethylamino-2-methylpropoxy)phenyl]-1H-pyrazolo[3,4-b]pyridine 1-[3-(2-Dimethylamino-1-methylethoxy)phenyl]-3-phenyl-1H-pyrazolo[3,4-b]pyridine·maleate, m.p. 118°–120° C.

2-(4-Methylphenyl)-3-[4-(2-dimethylamino-2-methylethoxy)phenyl]-1H-pyrazolo[3,4-b]pyridine·maleate, m.p. 126°–128° C.

1-[3-(2-Dimethylamino-2-methylethoxy)phenyl]-3-phenyl-1H-pyrazolo[3,4-b]pyridine·3/2 fumarate, m.p. 139°–142° C.

3-(4-Fluorophenyl)-1-[3-(2-dimethylamino-1-methylethoxy)phenyl]-1H-pyrazolo[3,4-b]pyridine·fumarate, m.p. 148°–149° C.

3-(4-Fluorophenyl)-1-[3-(2-dimethylamino-2-methylethoxy)phenyl]-1H-pyrazolo[3,4-b]pyridine·3/2 fumarate, m.p. 174°–176° C.

3-(4-Chlorophenyl)-1-[3-(2-dimethylamino-1-methylethoxy)phenyl]-1H-pyrazolo[3,4-b]pyridine·fumarate, m.p. 150°–152° C.

3-(4-Chlorophenyl)-1-[3-(2-dimethylamino-2-methylethoxy)phenyl]-1H-pyrazolo[3,4-b]pyridine·3/2 fumarate, m.p. 148°–150° C.

1-[3-(3-Dimethylamino-2-methylpropoxy)phenyl]-1-phenyl-1H -pyrazolo(3,4-b)pyridine·maleate·2/5 ethyl acetate solvate, m.p. 58°–60° C.

1-(2-Hydroxyethyl)-3-[4-(3-dimethylaminopropoxy)phenyl]-1H-pyrazolo[3,4-b]pyridine·½ fumarate, m.p. 162°–163° C.

1-(2-Acetoxyethyl)-3-[4-(3-dimethylaminopropoxy)phenyl]-1H-pyrazolo[3,4-b]pyridine·fumarate, m.p. 122°–124° C.

N-methyl-3-[4-(3-dimethylaminopropoxy)phenyl]-1H-pyrazolo-3,4-b]pyridin-1-ylacetamide·2 fumarate, m.p. 102°–105° C.

Methyl 6-{3-[4-(3-dimethylaminopropoxy)phenyl]-1H-pyrazolo-3,4-b]pyridin-1-yl}hexanate,
NMR(CDCl₃) δ: 1.33–2.70 (m, 12H), 2.24 (s, 6H), 3.60 (s, 3H), 4.07 (t, 2H), 4.53 (t, 2H), 6.93–8.51 (7H)

Ethyl 3-[4-(2-dimethylaminoethoxy)phenyl]-1H-pyrazolo-3,4-b]pyridin-1-ylacetate·maleate, m.p. 138°–140° C.

Ethyl 4-{3-[4-(3-dimethylaminopropoxy)phenyl]-1H-pyrazolo-3,4-b]pyridin-1-yl}acetate·2 fumarate, m.p. 121°–124° C.

Ethyl 3-{3-[4-(3-dimethylaminopropoxy)phenyl]-1H-pyrazolo-[3,4-b]pyridin-1-yl}propionate·fumarate, m.p. 105°–107° C.

Ethyl 2-methyl-2-{3-[4-(3-dimethylaminopropoxy)phenyl]-1H-pyrazolo[3,4-b]pyridin-1-yl}propionate,
NMR(CDCl₃)δ:1.10 (t, 3H), 2.03 (s, 6H), 1.96–2.40 (m, 2H), 2.30 (s, 6H), 2.52 (t, 2H), 4.01 (t, 2H), 4.12 (q, 2H), 6.98–8.51 (7H)

Ethyl 3-[4-(2-dimethylamino-1-methylethoxy)phenyl]-1H-pyrazolo[3,4-b]pyridin-1-ylacetate,
NMR(CDCl₃) δ: 1.25 (t, 3H), 1.33 (d, 3H), 2.33 (s, 6H), 2.34–2.78 (m, 2H), 4.21 (q, 2H), 4.55 (q, 1H), 5.26 (s, 2H), 6.98–8.51 (7H)

EXAMPLE 59

In 400 ml of dimethylformamide were suspended 39.3 g of 3-(4-hydroxyphenyl)-1-phenyl-1H-pyrazolo[3,4-b]pyridine, 34.4 g of ethyl bromoacetate and 28.4 g of potassium carbonate. The mixture was stirred under heating at 70° C. for 2 hours. The reaction mixture was concentrated under reduced pressure and the residue was extracted with benzene-water. The organic layer was concentrated. Hexane was added to the residue for crystallization. The obtained crude crystals were recrystallized from isopropyl ether to give 28 g of ethyl 4-(1-phenyl-1H-pyrazolo[3,4-b]pyridin-3-yl)phenoxyacetate, m.p. 118°–120° C.

EXAMPLE 60

In 300 ml of water was dissolved 5.1 g of sodium hydroxide, and 800 ml of ethanol was added to the solution. While stirring, thereto was added a solution of 40 g of ethyl 4-(1-phenyl-1H-pyrazolo[3,4-b]pyridin-3-yl)phenoxyacetate dissolved in 200 ml of dioxane. After the mixture was stirred at room temperature for 4 hours, it was poured into about 3 l of cold water. The mixture was neutralized by the addition of dilute hydrochloric acid. The resulting crystals were collected by filtration and recrystallized from hydrous dioxane to give 22.1 g of 4-(1-phenyl-1H-pyrazolo[3,4-b]pyridin-3-yl)phenoxyacetic acid, m.p. 220°–222° C.

EXAMPLE 61

In 200 ml of dimethylformamide were suspended 20 g of 3-(4-fluorophenyl)-1-(3-hydroxyphenyl)-1H-pyrazolo[3,4-b]pyridine, 21.9 g of bromoacetate and 18.1 g of potassium carbonate. The mixture was stirred at 65° C. for 4 hours. The reaction mixture was concentrated under reduced pressure. The residue was extracted with ethyl acetate-water. The organic layer was concentrated. Hexane was added to the residue for crystallization. The obtained crude crystals were recrystallized from isopropyl ether to give 10.9 g of ethyl 3-[3-(4-fluorophenyl)-1H-pyrazolo[3,4-b]pyridin-1-yl]phenoxyacetate, m.p. 130°–131° C.

EXAMPLE 62

In 5 ml of water was dissolved 0.97 g of sodium hydroxide, whereto 100 ml of ethanol was added. Thereto was added a solution of 8.0 g of ethyl 3-[3-(4-fluorophenyl)-1H-pyrazolo[3,4-b]pyridin-1-yl]phenoxyacetate dissolved in 60 ml of dioxane while stirring. After the mixture was stirred at room temperature for 4 hours, about 500 ml of water was added thereto and the mixture was neutralized with dilute hydrochloric acid. The resulting crystals were collected by filtration and recrystallized from dioxane to give 4.8 g of 3-[3-(4-fluorophenyl)-1H-pyrazolo[3,4-b]pyridin-1-yl]phenoxyacetic acid, m.p. 225°–226° C.

By conducting reactions and treatments in the same manner as in the above-mentioned Examples 61 and 62, the following compounds can be obtained.

Ethyl 4-(3-phenyl-1H-pyrazolo[3,4-b]pyridin-1-yl)phenoxyacetate 4-(3-phenyl-1H-pyrazolo[3,4-b]pyridin-1-yl)phenoxyacetic acid

EXAMPLE 63

To a mixture of 6 g of 3-[4-(3-dimethylaminopropoxy)phenyl]-1H-pyrazolo[3,4-b]pyridine, 2.3 g of triethylamine and 60 ml of chloroform was added 5.2 g of anhydrous propionic acid. The mixture was stirred at 55° C. for 4 hours. After cooling, water was added to the mixture. The chloroform layer was washed with dilute sodium hydrogen carbonate, and chloroform was distilled off. By addition of fumaric acid and recrystallization from ethanol, there was obtained 3-[4-(3-dimethylaminopropoxy)phenyl]-1-propionyl-1H-pyrazolo[3,4-b]pyridine·3/2 fumarate, m.p. 155°–157° C.

EXAMPLE 64

To a solution of 90 mg of ethanol, 40 ml of water and 2.0 g of sodium hydroxide was added 13 g of ethyl 3-[4-(3-dimethylaminopropoxy)phenyl]-1H-pyrazolo[3,4-b]pyridin-1-ylacetate. The mixture was stirred at room temperature for 2 hours. After the completion of the reaction, the reaction mixture was adjusted to pH 7 by dilute hydrochloric acid. The mixture was purified with ion-exchange resin (Diaion HP-20) and recrystallized from hydrous methanol to give 3-[4-(3-dimethylaminopropoxy)phenyl]-1H-pyrazolo[3,4-b]pyridin-1-ylacetic acid, m.p. 221°–223° C.

EXAMPLE 65

To a suspension of 9 g of 3-[4-(3-dimethylaminopropoxy)phenyl]-1H-pyrazolo[3,4-b]pyridine, 30 ml of dimethylformamide and 6.2 g of potassium carbonate was added dropwise 6.6 g of benzyl chloroacetate at 50° C. over the period of 2 hours. The mixture was kept at the same temperature for 4 hours. After the completion of the reaction, the reaction mixture was cooled. Water was added thereto, and the mixture was extracted with toluene. The extract was washed with water. After toluene was distilled off, diisopropyl ether was added to the residue for crystallization. The resulting crystals were recrystallized from diisopropyl ether - ethyl acetate to give benzyl 3-[4-(3-dimethylaminopropoxy)phenyl]-1H-pyrazolo[3,4-b]pyridin-1-ylacetate, m.p. 90°–92° C.

Hydrogen gas was blown into a suspension of 2.2 g of the benzyl ester compound, 10 ml of water, 30 ml of ethanol and 0.3 g of 5% palladium-carbon under stirring at room temperature under ordinary pressure. After the catalyst was filtered off, the filtrate was concentrated to dryness. The residue was recrystallized from hydrous methanol to give 3-[4-(3-dimethylaminopropoxy)phenyl]-1H-pyrazolo[3,4-b]pyridin-1-ylacetic acid, m.p. 221°–223° C.

EXAMPLE 66

(1) A mixture of 120 g of 2-chloro-3-[4-(1-methyl-2-dimethylaminoethoxy)benzoylpyridine and 700 ml of hydrazine-monohydrate and pyridine was refluxed for 18 hours. After pyridine was distilled off, water was added to the residue. The resulting crystals were collected by filtration, washed with water and then recrystallized from hydrous methanol to give 3-[4-(1-methyl-2-dimethylaminoethoxy)phenyl]-1H-pyrazolo[3,4-b]pyridine, m.p. 130°–132° C.

(2) In 40 ml of toluene was suspended 2.3 g of 60% sodium hydride, and 40 ml of dimethylformamide was added to the suspension under ice-cooling. Thereto was added in the two or three times divided manner 14.8 g of 3-[4-(1-methyl-2-dimethylaminoethoxy)phenyl]-1H-pyrazolo[3,4-b]pyridine. After the mixture was stirred for 15 minutes, a solution of 7.0 g of ethyl chloroacetate in 70 ml of toluene was added dropwise. The mixture was stirred at room temperature for 1 hour, and then it was stirred at 40° C. for 1 hour. After cooling, water was added. The toluene layer was separated, washed with water and dried. Toluene was distilled off. The residue was purified by chromatography to give ethyl 3-[4-(1-methyl-2-dimethylaminoethoxy)phenyl]-1H-pyrazolo[3,4-b]-pyridin-1-ylacetate in an oily form.

NMR(CDCl$_3$)δ:1.25 (t, 3H), 1.33 (d, 3H), 2.33 (s, 6H), 2.34–2.78 (m, 2H), 4.21 (q, 2H), 4.55 (q, 1H), 5.26 (s, 2H), 6.98–8.51 (7H)

(3) In 50 ml of methanol was dissolved 12 g of the thus-obtained compound. A solution of 1.38 g of sodium hydroxide in 10 ml of water was added to said solution. The mixture was stirred at room temperature for 1 hour. The reaction mixture was adjusted to pH 7 with dilute hydrochloric acid. Methanol was distilled off. The residue was purified by ionexchange resin (Diaion PH-20) and recrystallized from hydrous isopropyl alcohol. Ethanol was added to the thus-obtained crystals, and the mixture was heated to give 3-[4-(1-methyl-2-dimethylaminoethoxy)phenyl]-1H-pyrazolo[3,4-b]pyridin-1-ylacetic acid, m.p. 210°–211° C.

The following compounds can be obtained in the same manner as in Examples 64–66.

2-Methyl-2-{3-[4-(3-dimethylaminopropoxy)phenyl]-1H-pyrazolo[3,4-b]pyridin-1-yl}propionic acid, m.p. 187°–190° C.

3-{3-[4-(3-Dimethylaminopropoxy)phenyl]-1H-pyrazolo[3,4-b]-pyridin-1-yl}propionic acid·½ hydrate, m.p. 86°–90° C.

6-{3-[4-(3-Dimethylaminopropoxy)phenyl]-1H-pyrazolo[3,4-b]-pyridin-1-yl}hexanoic acid, m.p. 96°–100° C.

EXAMPLE 67

To a mixture of 6 g of 3-[4-(2-dimethylaminoethylamino)phenyl]-1H-pyrazolo[3,4-b]pyridine, 5 g of potassium carbonate and 60 ml of dimethylformamide was added dropwise 4.6 g of ethyl chloroacetate. The mixture was stirred at 50° C. for 4 hours. After the solvent was distilled off, the residue was dissolved in ethyl acetate and washed with water. After ethyl acetate was distilled off, the residue was purified by column chromatography to give ethyl 3-[4-(2-dimethylaminoethylamino)phenyl]-1H-pyrazolo[3,4-b]pyridin-1-ylacetate in an oily form.

NMR(CDCl$_3$)δ:1.20 (t, 3H), 2.40 (s, 6H), 2.56 (t, 2H), 3.20 (t, 2H), 4.20 (q, 2H), 5.30 (s, 2H), 6.63–8.56 (7H)

EXAMPLE 68

By conducting reactions and treatments in the same manner as in Example 66 (3), using 4.6 g of ethyl 3-[4-(2dimethylaminoethylamino)phenyl]-1H-pyrazolo[3,4-b]pyridin-1-ylacetate and 0.65 g of sodium hydroxide and recrystallizing from hydrous methanol, there was obtained 3-[4-(2-dimethylaminoethylamino)phenyl]-1H-pyrazolo[3,4-b]pyridin-1-ylacetic acid, m.p. 240°–242° C.

EXAMPLE 69

(1) In 300 ml of trifluoroacetic acid was dissolved 58.3 g of 1-(4-aminophenyl)-3-phenyl-1H-pyrazolo[3,4-b]pyridine. Thereto, 51.3 g of trifluoroacetic anhydride was added dropwise under ice-cooling. The mixture was stirred at room temperature for 2 hours. After trifluoroacetic acid was distilled off under reduced pressure, water was added to the residue. The mixture was extracted with ethyl acetate and washed with water. Ethyl acetate was distilled off, and isopropyl ether was added to the residue for crystallization to give 3-phenyl-1-(4-trifluoroacetylaminophenyl)-1H-pyrazolo[3,4-b]pyridine, m.p. 172°–174° C.

(2) In 160 ml of acetone were suspended 8 g of 3-phenyl-1-(4-trifluoroacetylaminophenyl)-1H-pyrazolo[3,4-b]pyridine, 3.4 g of 2-dimethylaminoethylchloride, 11.6 g of potassium carbonate and 0.5 g of potassium iodide. The mixture was stirred under reflux for 24 hours. After cooling, insoluble matters were filtered off and acetone was distilled off. The obtained residue was dissolved in 100 ml of methanol, whereto 35 ml of 14% ammonia water was added. The mixture was refluxed for 25 hours for hydrolysis. After methanol was distilled off, the residue was dissolved in ethyl acetate. The solution was washed with water. After ethyl acetate was distilled off and the residue was purified by column chromatography, the product was converted into its maleate, which was recrystallized from ethyl acetate - methanol to give 1-[4-(2-dimethylaminoethylamino)phenyl]-3-phenyl-1H-pyrazolo[3,4-b]-pyridine·maleate·½ hydrate, m.p. 80°–88° C.

EXAMPLE 70

By conducting reactions and treatments in the same manner as in Example 69 (2), using 10 g of 3-phenyl-1-(4-trifluoroacetylaminophenyl)-1H-pyrazolo[3,4-b]pyridine and 4.8 g of 3-dimethylaminopropyl chloride, and recrystallizing from ethyl acetate-isopropyl alcohol, there was obtained 1-[4-(3-dimethylaminopropylamino)phenyl]-3-phenyl-1H-pyrazolo[3,4-b]pyridine·2 maleate, m.p. 145°–146° C.

EXAMPLE 71

Formulation Example

The tablets which contain 10 mg of the compound of the present invention per tablet can be prepared in accordance with the following prescription.

| Compound of Example 1 | 10.0 mg |
|---|---|
| Lactose | 58.5 mg |
| Corn starch | 25.0 mg |
| Crystalline cellulose | 20.0 mg |
| Polyvinylpyrrolidone K-30 | 2.0 mg |
| Talc | 4.0 mg |
| Magnesium stearate | 0.5 mg |
| | 120.0 mg |

The compound was pulverized by atomizer into fine powders of mean particle diameter of not more than 10μ, which were admixed thoroughly with lactose, corn starch and crystalline cellulose in a kneading machine, followed by kneading with the use of a paste of polyvinylpyrrolidone. The kneaded mixture was passed through a sieve of 200 mesh, dried at 50° C. and then passed through a sieve of 24 mesh. Talc and magnesium stearate were mixed with said mixture. The mixture was compressed into tablets weighing 120.0 mg per tablet with the use of a pounder of diameter of 8 mm. These tablets can be, if desired, subjected to sugar-coating and film-coating treatment.

The present invention has been described suitably and sufficiently by the foregoing specification including examples, which can be varied or modified within the spirit and scope of this invention.

We claim:

1. A fused pyrazole compound of the formula

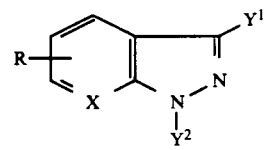

on a pharmaceutically acceptable salt thereof wherein in the above formula, X is $=N-$; R represents hydrogen, an alkyl group, an alkoxy group or a halogen; $Y^1$ represents a group of the formula:

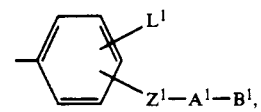

phenyl group or a phenyl group substituted by one to three halogen(s), alkyl group(s) and/or alkoxy group(s), and $Y^2$ represents a group of the formula:

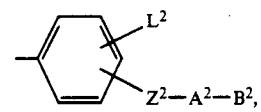

a group of the formula: $-A^2-B^2$, hydrogen, an alkyl group, a phenylalkyl group, a phenylalkyl group in which the phenyl nucleus is substituted by one to three halogen(s), alkyl group(s) and/or alkoxy group(s), phenyl group or a phenyl group substituted by one to three halogen(s), alkyl group(s) and/or alkoxy group(s), an alkoxyalkyl group, wherein either $Y^1$ or $Y^2$ represents or both of $Y^1$ and $Y^2$ represent a group of the formula:

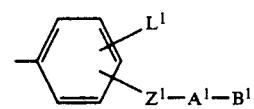

or of the formula:

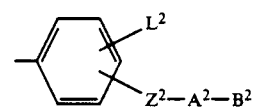

wherein, $Z^1$ and $Z^2$ are the same or different, and respectively represent $-O-$, $-S-$ or $-NR^3$ (wherein $R^3$ represents hydrogen or an alkyl group); $A^1$ and $A^2$ are the same or different, and respectively represent an alkylene group; $B^1$ and $B^2$ are the same or different, and respectively represent carboxyl group, an alkoxycarbonyl group, a phenylalkoxycarbonyl group (in which the phenyl nucleus may be substituted by one to three halogen(s), alkyl group(s), and/or alkoxy group(s)), an acyl group, hydroxy group, an acyloxy group or a group of the formula:

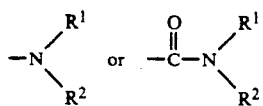

(wherein $R^1$ and $R^2$ are the same or different and respectively represent hydrogen, an alkyl group, a dialkylaminoalkyl group or a hydroxyalkyl group or represent a group which combinedly forms, together with the adjacent nitrogen atom, a heterocycle) and $L^1$ and $L^2$ are the same or different and respectively represent hydrogen, a halogen, an alkyl group or an alkoxy group.

2. The compound as claimed in claim 1 wherein at least one of $Z^1$ and $Z^2$ is oxygen.

3. A compound as claimed in claim 1 which is selected from a group consisting of 3-[4-(1-methyl-2-dimethylaminoethoxy)phenyl]-1H-pyrazolo[3,4-b]pyridin-1-ylacetic acid, ethyl 3-[4-(1-methyl-2-dimethylaminoethoxy)phenyl]-1H-pyrazolo[3,4-b]pyridin-1-ylacetate, 3-[4-(3-dimethylaminopropoxy)phenyl]-1H-pyrazolo[3,4-b]pyridin-1-ylacetic acid, ethyl 3-[4-(2-dimethylaminoethoxy)phenyl]-1H-pyrazolo[3,4-b]pyridin1-ylacetate, 1-[4-(3-dimethylaminopropoxy)phenyl]-3-phenyl-1H-pyrazolo[3,4-b]pyridine, 1-[3-(2-methyl-3-dimethylaminopropoxy)phenyl]-3-phenyl-1H-pyrazolo[3,4-b]pyridine, 1-(4-methylphenyl)-3-[4-(3-dimethylaminopropoxy)phenyl]-1H-pyrazolo[3,4-b]pyridine, 1-[3-(2-dimethylaminoethoxy)phenyl]-3-[4-(2-dimethylaminoethoxy)phenyl]-1H-pyrazolo[3,4-b]pyridine, N-(2-diethylaminoethyl)-3-[3-(4-fluorophenyl)-1H-pyrazolo[3,4-b]pyridin-1-yl]phenoxyacetamide and 3-{3-[4-(3-dimethylaminopropoxy)phenyl]-1H-pyrazolo[3,4-b]pyridin-1-yl}propionic acid and their pharmaceutically acceptable salts.

4. A pharmaceutical composition which comprises as the effective ingredient the compound as claimed in claim 1 and a pharmacologically acceptable carrier.

* * * * *